(12) United States Patent
Tenne et al.

(10) Patent No.: US 9,155,595 B2
(45) Date of Patent: Oct. 13, 2015

(54) ENDODONTIC FILES AND METHOD OF PREPARATION THEREOF

(75) Inventors: Reshef Tenne, Rehovot (IL); Meir Redlich, Tel Aviv (IL); Adi Ram-Adini, Rehovot (IL); Yishay Feldman, Rehovot (IL); Gili Naveh, Rehovot (IL); Joshua Moshonov, Tel Aviv (IL); Boaz Shay, Petach Tikva (IL)

(73) Assignees: YEDA RESEARCH AND DEVELOPMENT CO. LTD., Rehovot, IL (US); HADASIT MEDICAL RESEARCH SERVICES & DEVELOPMENT LTD., Jerusalem, IL (US)

(*) Notice: Subject to any disclaimer, the term of this patent is extended or adjusted under 35 U.S.C. 154(b) by 63 days.

(21) Appl. No.: 13/806,495

(22) PCT Filed: Jun. 21, 2011

(86) PCT No.: PCT/IL2011/000493
§ 371 (c)(1),
(2), (4) Date: Mar. 11, 2013

(87) PCT Pub. No.: WO2011/161676
PCT Pub. Date: Dec. 29, 2011

(65) Prior Publication Data
US 2013/0177871 A1    Jul. 11, 2013

Related U.S. Application Data

(60) Provisional application No. 61/356,720, filed on Jun. 21, 2010.

(51) Int. Cl.
*A61C 5/02*    (2006.01)

(52) U.S. Cl.
CPC ............ *A61C 5/023* (2013.01); *A61C 2201/007* (2013.01)

(58) Field of Classification Search
CPC .......................... A61C 5/023; A61C 2201/007
USPC ..................................................... 433/102, 224
See application file for complete search history.

(56) References Cited

U.S. PATENT DOCUMENTS 5,215,461 A * 6/1993 Riazi .............................. 433/224
5,868,570 A * 2/1999 Hickok et al. ................. 433/102
(Continued)

FOREIGN PATENT DOCUMENTS

WO    2006123336 A2    11/2006

OTHER PUBLICATIONS

Morgan, N. B., Medical shape memory alloy applications—the market and its products, Materials Science and Engineering, 2004, pp. 16-23, vol. 378 No. 1-2, Elsevier B.V.
(Continued)

*Primary Examiner* — Cris L Rodriguez
*Assistant Examiner* — Hao D Mai
(74) *Attorney, Agent, or Firm* — Pearl Cohen Zedek Latzer Baratz LLP; Mark S. Cohen (57) ABSTRACT

The present invention provides a selective coating of an endodontic file, in which the distal end of the file is uncoated or alternatively leaving the outermost part of the blades of the distal end portion uncoated. The distribution of the nanoparticles is thus non uniform along the surface of the file leaving only a part of the file coated. In the present invention, the distal end of the device being subjected to the highest torque is either uncoated at all, or has a coated core and uncoated blades.

16 Claims, 9 Drawing Sheets

(56) References Cited

U.S. PATENT DOCUMENTS

| | | | | |
|---|---|---|---|---|
| 6,409,506 | B1* | 6/2002 | Graybill | 433/102 |
| 6,575,747 | B1* | 6/2003 | Riitano et al. | 433/102 |
| 6,910,889 | B1* | 6/2005 | Hickok | 433/119 |
| 2007/0015107 | A1* | 1/2007 | Mannschedel et al. | 433/102 |
| 2007/0284255 | A1 | 12/2007 | Gorokhovsky et al. | |
| 2009/0032499 | A1* | 2/2009 | Tenne et al. | 216/109 |
| 2010/0105004 | A1* | 4/2010 | Levy et al. | 433/102 |
| 2013/0040261 | A1* | 2/2013 | Kwon et al. | 433/102 |

OTHER PUBLICATIONS

Pelton, A. R., et al., Nitinol Medical Devices, Advanced Materials & Processes, 2005, pp. 63-65, vol. 163, No. 10, Advanced Materials & Processes.

Thompson, S. A., An overview of nickel-titanium alloys used in dentistry, International Endodontic Journal, 2000, pp. 297-310, vol. 33, No. 4, Blackwell Science Ltd.

Peters, O. A., Current Challenges and Concepts in the Preparation of Root Canal System: A Review, Journal of Endodontics, 2004, pp. 559-567, vol. 30, No. 8, The American Association of Endodontists.

Otsuka, K. and Ren, X., Physical metallurgy of Ti-Ni-based shape memory alloys, Progress in Materials Science, 2005, pp. 511-678, vol. 50, No. 5, Elsevier Ltd.

Bojda, O., et al., Precipitation of Ni4Ti3-variants in a polycrystalline Ni-rich NiTi shape memory alloy, Scripta Materialia, 2005, pp. 99-104, vol. 53, No. 1, Elsevier Ltd.

Eggeler, G., et al., Structural and functional fatigue of NiTi shape memory alloy, Materials Science and Engineering, A, 2004, pp. 24-33, vol. 378, Elsevier B.V.

Liu, Y. N. and Tan, G. S., Effect of deformation by stress-induced martensitic transformation on the transformation behaviour of NiTi, Intermetallics, 2000, pp. 67-75, vol. 8, Elsevier B.V.

Yared, G. M., et al., Influence of rotational speed, torque and operator's proficiency on ProFile failures, International Endodontic Journal, 2001, pp. 47-53, vol. 34, Blackwell Science Ltd.

Parashos, P., et al., Rotary NiTi Instrument Fracture and its Consequences, Journal of Endodontics, 2006, pp. 1031-1043, vol. 32, No. 1, 1031-1043.

Nayan, N., et al., Effect of mechanical cycling on the stress-strain response of a martensitic Nitinol shape memory alloy, Materials Science and Engineering, A, 2009 pp. 60-67, vol. 525, Elsevier B.V.

Sattapan, B., et al., Defects in Rotary Nickel-Titanium Files after Clinical Use, Journal of Endodontics, 2000, pp. 161-165, vol. 26, No. 3, The American Association of Endodontists.

Kuhn, G., et al., Influence on Structure of Nickel-Titanium Edodontic Instruments Failure, Journal of Endodontics, 2001, pp. 516-520, vol. 27, No. 8, The American Association of Endodontists.

Cheung, G. S. P., et al., Defects in ProTaper S1 instruments after clinical use: fractographic examination, International Endodontic Journal, 2005, pp. 802-809, vol. 38.

Rapoport, L. et al., Hollow nanoparticles of WS2 as potential solid-state lubricants, Nature, 1997, pp. 791-793, vol. 387, Macmillan Publishers Ltd.

Rapoport, L., et al., Applications of WS2 (MoS2) inorganic nanotubes and fullerene-like nanoparticles for solid lubrication and for structural nanocomposites, Journal of Materials Chemistry, 2005, pp. 1782-1788, vol. 15, The Royal Society of Chemistry.

Tenne, R., et al., Polyhedral and cylindrical structures of tungsten disulphide, Nature, 1992, pp. 444-446, vol. 360, Research Library Core.

Pelletier, H., et al., Structural and mechanical characterisation of boron and nitrogen implanted NiTi shape memory alloy, Surface & Coatings Technology, 2002, pp. 309-317, vol. 158-159, Elsevier B.V.

Spanaki-Voreadi, A. P., et al, Failure mechanism of ProTaper Ni-Ti rotary instruments during clinical use: fractographic analysis, International Endodontic Journal, 2006, pp. 171-178, vol. 39: 171-178.

Alapati, S. B. et al., SEM Observations of Nickel-Titanium Rotary Endodontic Instruments that Fractured During Clinical Use, Journal of Endodontics, 2005, pp. 40-43, vol. 31, No. 1, The American Association of Endodontists, United States.

Brinson, L. C., et al., Stress-induced transformation behavior of a polycrystalline NiTi shape memory alloy: micro and macromechanical investigations via in situ optical microscopy, Journal of the Mechanics and Physics of Solids, 2004, pp. 1549-1571, vol. 52, Elsevier Ltd.

Friedman, H., et al., Fabrication of self-lubricating cobalt coatings on metal surfaces, Nanotechnology, 2007, pp. 1-8, vol. 18, IOP Publishing Ltd, United Kingdom.

Kim H. C., et al., Cyclic Fatigue and Fracture Characteristics of Ground and Twisted Nickel-Titanium Rotary Files, Journal of Endodontics, 2010, pp. 147-152, vol. 36, No. 1, The American Association of Endodontists.

Zhang E. W., et al., Influence of cross-sectional design and dimension on mechanical behavior of nickel-titanium instruments under torsion and bending: a numerical analysis, Journal of Endodontics, 2010, pp. 1394-1398, vol. 36, No. 8, American Association of Endodontists.

Condorelli, G. G., et al., Improvement of the fatigue resistance of NiTi endodontic files by surface and bulk modifications, International Endodontic Journal, 2010, pp. 866-873, vol. 43.

Anderson, M. E., et al., Fracture resistance of electropolished rotary nickel-titanium endodontic instruments, Journal of Endodontics, 2007, pp. 1212-1216, vol. 33, No. 10.

Peters, O. A, et al., Effect of liquid and paste-type lubricants on torque values during simulated rotary root canal instrumentation, International Endodontic Journal, 2005, pp. 223-229, vol. 38.

Park, S. Y., et al., Dynamic Torsional Resistance of Nickel-Titanium Rotary Instruments, Journal of Endodontics., 2010, pp. 1200-1204, vol. 36, No. 7, American Association of Endodontists.

Ram Adini, A., et al., Alleviating fatigue and failure of NiTi endodontic files by a coating containing inorganic fullerene-like WS2 nanoparticles, Journal of Materials Research, 2011., vol. 26, No. 10, Materials Research Society.

* cited by examiner

| Element | Atomic% |
|---------|---------|
| O | 28.41 |
| S | 7.00 |
| Cl | 1.78 |
| Ti | 2.91 |
| Co | 55.38 |
| W | 4.52 |

ENDODONTIC FILES AND METHOD OF PREPARATION THEREOF

CROSS-REFERENCE TO RELATED APPLICATIONS

This application is a National Phase Application of PCT International Application No. PCT/IL2011/000493, International Filing Date Jun. 21, 2011, claiming priority of U.S. Provisional Application Ser. No. 61/356,720 filed Jun. 21, 2010, which are hereby incorporated by reference.

FIELD OF THE INVENTION

This invention is generally in the field of dental appliances, and relates to endodontic files and method of manufacture thereof.

REFERENCES

The following references are considered to be pertinent for the purpose of understanding the background of the present invention:

[1] Morgan, N. B., *Materials Science and Engineering a-Structural Materials Properties Microstructure and Processing* 378 (1-2), 16 (2004).
[2] Pelton, A. R. et al., *Advanced Materials & Processes* 163 (10), 63 (2005).
[3] Thompson, S. A., *International Endodontic Journal* 33 (4), 297 (2000).
[4] Peters, O. A., *Journal of Endodontics* 30 (8), 559 (2004).
[5] Otsuka, K. and Ren, X., *Progress in Materials Science* 50 (5), 511 (2005).
[6] Bojda, O., Eggeler, G., and Dlouhy, A., *Scripta Materialia* 53 (1), 99 (2005).
[7] Eggeler, G. et al., *Materials Science and Engineering a-Structural Materials Properties Microstructure and Processing* 378 (1-2), 24 (2004).
[8] Liu, Y. N. and Tan, G. S., *Intermetallics* 8 (1), 67 (2000).
[9] Yared, G. M., Dagher, F. E. B., and Machtou, P., *International Endodontic Journal* 34 (1), 47 (2001).
[10] Parashos, P. and Messer, H. H., *Journal of Endodontics* 32 (11), 1031 (2006).
[11] Nayan, N., Buravalla, V., and Ramamurty, U., *Materials Science and Engineering a-Structural Materials Properties Microstructure and Processing* 525 (1-2), 60 (2009).
[12] Kuhn, G., Tavernier, B., and Jordan, L., *Journal of Endodontics* 27 (8), 516 (2001).
[13] Sattapan, B., Nervo, G. J.; Palamara, J. E. A., and Messer, H. H., Defects in rotary nickel-titanium files after clinical use *Journal of Endodontics* 26 (3), 161-165 (2000).
[14] Cheung, G. S. P. et al., *International Endodontic Journal* 38 (11), 802 (2005).
[15] Rapoport, L. et al., *Nature* 387 (6635), 791 (1997).
[16] Rapoport, L., Fleischer, N., and Tenne, R., *Journal of Materials Chemistry* 15 (18), 1782 (2005).
[17] Tenne, R., Margulis, L., Genut, M., and Hodes, G., *Nature* 360 (6403), 444 (1992).
[18] Pelletier, H., Muller, D., Mille, P., and Grob, J. J., Structural and mechanical characterisation of boron and nitrogen implanted NiTi shape memory alloy. *Surface & Coatings Technology* 158, 309-317 (2002).
[19] Spanaki-Voreadi, A. P., Kerezoudis, N. P., and Zinelis, S., *International Endodontic Journal* 39 (3), 171 (2006).
[20] Alapati, S. B. et al., *Journal of Endodontics* 31 (1), 40 (2005).
[21] Brinson, L. C., Schmidt, I., and Lammering, R., *Journal of the Mechanics and Physics of Solids* 52 (7), 1549 (2004).
[22] Friedman, H. et al., *Nanotechnology* 18 (11) (2007).
[23] Kim H C, Yum J, Hur B, Cheung G S P. Cyclic Fatigue and Fracture Characteristics of Ground and Twisted Nickel-Titanium Rotary Files. Journal of Endodontics; 36(1):147-152 (2010).
[24] Zhang E-W, Cheung G S P, Zheng Y-F. Influence of cross-sectional design and dimension on mechanical behavior of nickel-titanium instruments under torsion and bending: a numerical analysis. J Endod; 36(8):1394-1398 (2010).
[25] Condorelli G G, Bonaccorso A, Smecca E, Schafer E, Cantatore G, Tripi T R. Improvement of the fatigue resistance of NiTi endodontic files by surface and bulk modifications. International Endodontic Journal; 43(10):866-873 (2010).
[26] Anderson M E, Price J W H, Parashos P. Fracture resistance of electropolished rotary nickel-titanium endodontic instruments. Journal of Endodontics 2007; 33:1212-1216.
[27] Peters O A, Boessler C, Zehnder M. Effect of liquid and paste-type lubricants on torque values during simulated rotary root canal instrumentation. International Endodontic Journal 2005; 38(4):223-229.
[28] Park S Y, Cheung G S P, Yum J, Hur B, Park J K, Kim H C. Dynamic Torsional Resistance of Nickel-Titanium Rotary Instruments. Journal of Endodontics; 36(7):1200-1204 (2010).

BACKGROUND OF THE INVENTION

Figure 1A:
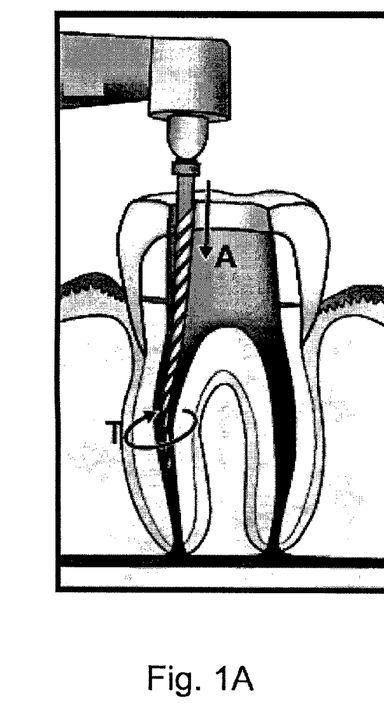
FIGS. 1A-1B are schematic representations of an endodontic file, while shaping and cleaning the root canal.
Figure 1B:
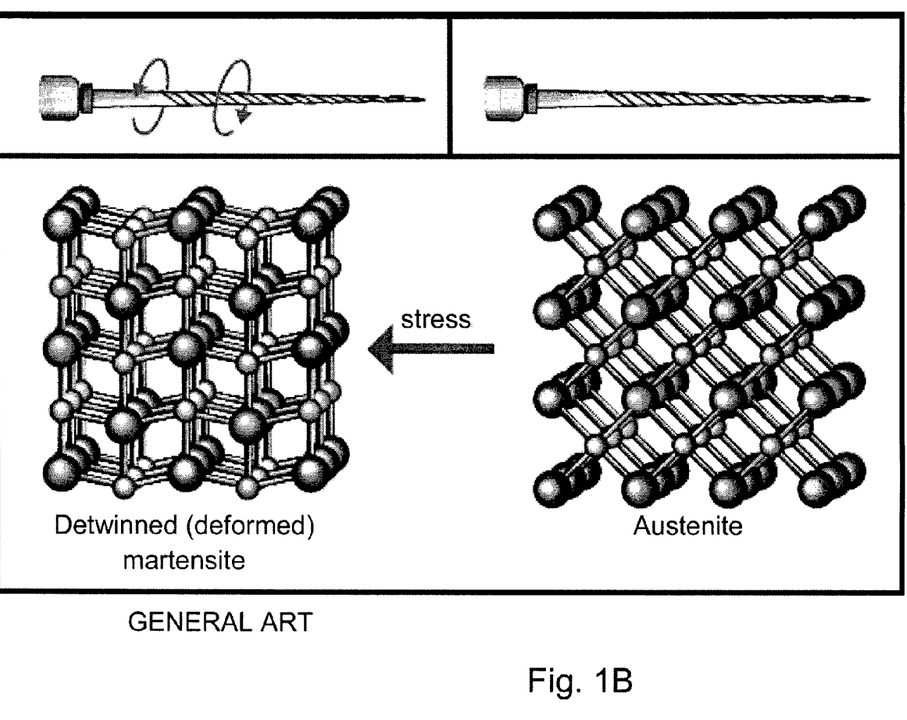

Shape memory (SMA) and superelastic alloys, such as NiTi (nitinol) are extensively used and explored for medical applications [1, 2]. These include among others cardiologic, orthopedics, laparoscopic surgeries, and dental applications [3]—e.g. endodontic files (EF) used for root canal treatment. In the last decade, NiTi rotary instruments have become an integral important adjunct in endodontics [4]. NiTi instruments have substantially reduced the incidence of several major clinical problems in endodontics, mainly by maintaining the original shape and curvature of the canal, thus, reducing the likelihood of procedural errors. As illustrated in FIGS. 1A-1B, the majority phase in rotary endodontic files is austenite. FIG. 1A schematically represents an endodontic file, while shaping and cleaning the root canal. In the figure, the vector represents the torque (T) when the file rotates clockwise; the vertical arrow (A) represents the direction of the apical force. FIG. 1B illustrates structural changes following austenite-martensite stress induced phase transformation. When the file is twisted, the chemical structure transforms from austenite (cubic structure) into martensite (monoclinic). The stressed file transforms to the (detwinned) martensite phase, which is more elastic. When the load on the file is removed, the NiTi files reversibly revert back to the austenite phase [3, 5]. This stress-induced phase transformation results in reversible strains as high as 8% (superelasticity) [3].

GENERAL DESCRIPTION

Many artificial devices (intracorporeal devices) and implants are inserted to the human body for different purposes and different periods of times. Many of the inserted devices are made of superelastic nickel-titanium (Nitinol-NiTi) shape memory alloys which can undergo fatigue and eventually total failure. Thus, failure of root canal files can lead to the tooth loss. Biofouling, i.e. sedimentation of body residues and bacteria jeopardizes the functionality of many of the long term implants, like titanium-based dental implants, leading to complications due to infection hazards. Thus, a common problem with NiTi devices is its catastrophic failure [6-7]. Cyclic loadings below the yield stress lead to some irreversible long-term processes in the NiTi alloys (fatigue) [6-8] and eventually to breakage. Indeed, occasional breakage of endodontic files during root canal treatment has been reported [9, 10]. Failing to remove the fractured segment may lead to infection and loss of the treated tooth.

During the course of endodontic treatment, a repetitive stress-induced phase transformation from austenite to martensite occurs in the file. These frequent phase changes lead to irreversible accumulation of defects and precipitates. Since the root canal has a curved shape, flexural (compression) stress influences these irreversible changes, too. This behavior manifests itself as a reduced elasticity and strength of the file [11-14], which may eventually lead to its failure.

In order for the file to go through the constricted space of the tortuous root canal, as illustrated in FIG. 1A, an apical force-pushing the file forward and torque-responsible for the rotary motion of the file must be applied. The classic literature regarding EFs distinguishes between two kinds of breakage—incidental (torsional) failure and fatigue related failure. The fatigue related failure was, up until recently, attributed to flexural fatigue, caused by the EF flexing back and forth when rotating at a flexed position. A recent work by Park et al. suggests that the fracture of NiTi rotary files is also attributed to torsional fatigue, due to repetitive locking and releasing (stick-slip) of the files during the clinical practice [28]. In addition to fatigue-based failure, file fracture may occur incidentally also due to locking of the twisted file in a constricted root canal and application of an excessive torque (termed taper lock or incidental failure) [13]. In this case, the applied torque exceeds the fracture strength of the file, leading thereby to immediate failure.

Finding a way to reduce file breakage during root canal treatment would have great beneficial influence on the costs of treatment and the prognosis of treated teeth, as well as a psychological effect on the practitioner who would be relieved of the fear of leaving a fractured segment in a treated tooth.

The strategy employed to increase the intrinsic fracture resistance of NiTi files is mainly based on improving the files' manufacturing process [23], modifying the file design and cross-section [24] or applying a surface treatment to the file [25]. Surface treatments such as nitridation and ion implantation [18] or electropolishing [26] improve the EF mechanical properties such as hardness and resistance to wear and fatigue. These methods are focused on hardening the EF, thus, making it less susceptible to breakage. In addition, the use of pastes or liquid irrigation media such as EDTA, chlorhexidine varnish and sodium hypochlorite during root canal treatment increase lubrication and helps drilling into the treated canal and disinfecting it [27].

The present invention provides a novel EF configuration. The invention is based on the inventors' understanding that appropriate friction distribution of the EF when in use is required to improve mechanical strength of the EF. This is achieved in the present invention by an appropriate selective coating of an EF body with nanostructures.

Coating of cutting tools is widespread in the tooling industry helping to improve the performance and durability of e.g. drills [18]. The inventors of the present invention have shown that providing cobalt coatings containing a low percentage of fullerene-like nanostructures, e.g. $WS_2$ nanoparticles (Co/IF) [15-17], leads to a remarkable reduction of the failure-rate of endodontic files in both taper-locked (incidental) and fatigue-induced modes. Dental implants being coated by friction reducing film comprising inorganic fullerene-like (IF) particles or composite containing IF particles reduces the torque required to install the implant by reducing the friction between the implant and the sidewalls of the bore as described for example in the International Patent Publication number WO 2006/123336. The addition of fullerenes-like nanostructures, solid lubricants, to the surface of the file as a permanent coating, thus reduces the friction between the NiTi file and the walls of the canal, without disturbing the unique characteristics of the shape memory alloy. The impregnation of IF—$WS_2$ nanoparticles as a coating of a NiTi file showed remarkable reduction in the torque under various conditions (drilling, etc.). Therefore, there is provided a friction reducing method having vast implication on the duration, safety and consequences of root canal treatment. This analysis is remarkable in so far as it demonstrates that a few micron thick Co/IF coating dramatically alter the bulk mechanical behavior of a device, improve the lifetime of the root canal file and minimize the hazard of its failure. Such coatings, may furthermore, offer an alternative to the current approach of adding lubricating agents during treatment. The present analysis bears on a large number of technologies based on NiTi SMA.

The addition of IF—NP onto NiTi medical appliances such as endodontic files reduces the fatigue accumulation of the alloy and thus, reduces the failure rate of NiTi instruments. Reducing the separation rate of NiTi files have vast implications on the treatment outcomes, on the patient and on the practitioner.

The present invention provides a selective coating of the file, in which the distal end (leading narrower part) of the file is uncoated or alternatively leaving the outermost part of the blades of the distal end portion uncoated. The distribution of the nanoparticles is thus not uniform along the surface of the file leaving only a part of the file coated. In the present invention, the distal end of the device being subjected to the highest torque is either uncoated at all, or has a coated core and uncoated blades. In this connection, it should be understood that root canals and their associated pulp chamber are the physical hollows within a tooth that are naturally inhabited by nerve tissue, blood vessels and other, inorganic/bio-organic hybrid and cellular entities. Endodontic therapy involves the removal of these structures, the subsequent cleaning, shaping, and decontamination of the hollows with tiny files and irrigating solutions. However, the canal has a certain curvature and a variable diameter. The canal is also usually obstructed by the infected pulp and a relatively high force should be applied to drill the file inside the canal. The inventors have provided an efficient EF having a distal end portion with a sufficient mechanical strength and flexibility to drill the pulp out of the canal and to define a path within the tortuous canal, while minimizing the risk of failure of the file during its insertion. The selected distribution of the nanostructures along the file surface enables to improve the strength of the file as well as reducing the friction force applied on the proximal end of the file and therefore the overall applied torque. Therefore, the novel configuration of the file of the present invention enables the reduction in friction without impairing the cutting (drilling) efficiency of the files. In this connection, it should be noted that when a file is subjected to fatigue, fatigue striation appears (shear bands due to martensite domains) beneath the surface of the file. The inventors have found that the torque applied on the file is not uniformly distributed on the circumference of files. The fatigue striations indicative of fatigue related failure were identified while examining the fractured area cross-section after the torsional fatigue test. The striations usually nucleate at the corners close to the file surface, where the file-canal-wall interaction is the strongest. Consequently, reducing the torque and making it more uniformly distributed on the file surface lead to a time-delay for nucleation of the striations which are associated with irreversible changes and fatigue.

Therefore, there is provided an endodontic file for root canal treatment. The endodontic file comprises an elongated integral body formed with blades defining a rotatable screw made member. The member is made of a shape memory and superelastic material composition, and has a distal end for penetration into the root canal and a proximal end through which a force is applied to the body to enable the penetration of the distal end. The screw member is formed with a coating of a material comprising metal or metal alloy and inorganic fullerene-like (IF) structures or a composite containing such nanostructures with a predetermined non-uniform distribution of the coating material along the member. The non-uniform distribution is selected for reducing failure rate of the file and file fracture under the application of the force through the proximal end.

By using the novel IF—NP coated EFs of the present invention, the inventors have shown that the friction coefficient was significantly reduced at the proximal end of the file while the friction coefficient was maintained sufficiently high at the distal end of the file to ensure adequate drilling capability. In the drilling industry, it is well established that reducing the friction during the drilling process leads to improved swarf removal; overall performance and longer lifetime of the used drill. Reduced friction manifests itself in a reduced drilling temperature, less attachment of debris to the tool, lower tool-wear and lower power consumption. Moreover, the drilling ability of the IF—NP coated EFs is not impaired by the partial coating process. Moreover, a lesser amount of torque is needed in order to drill an equivalent hole. In addition, coated EFs exhibited a significantly prolonged time to failure under torsional fatigue testing. Thus, the selective distribution of IF—NP to EFs has been shown to significantly improve several properties which are important to endodontic practice: the selective distribution of the friction coefficient, the selective distribution of the drilling torque and time to failure. Combined, these results indicate that these biocompatible materials may be successfully integrated in endodontic practice, thus reducing EF fracture and prolonging their lifespan.

In some embodiments, the non-uniform distribution of the coating material is selected such that a portion of the member at the distal end is uncoated, and a remaining portion of the member has the coating.

In other embodiments, the non-uniform distribution of the coating material is selected such that the blades within a portion of the screw member at the distal end are uncoated, while a remaining portion of the member has the coating. The nanostructures or the composite containing the nanoparticles reduces friction between the file and the canal, as compared to uncoated article. The portion at the distal end may have a length of about ⅓ of the entire screw member.

In some embodiments, the shape memory and superelastic material composition is selected from NiTi or from stainless steel.

In some embodiments, the coating has a thickness of between 0.3 micron and 10 microns.

In some embodiments, the coating material is selected from Ni—P—IF-nanoparticles, Co—P—IF-nanoparticles, Co—B—IF-nanoparticles, Ni—B—IF-nanoparticles, metal film containing IF-nanoparticles, polyurethane, polypropylene or epoxy containing IF-nanoparticles or a sol-gel glass containing IF-nanoparticles, Co—Ni—IF-nanoparticles, Cr—Co—IF-nanoparticles, TiN—IF-nanoparticles, TiON—IF-nanoparticles, Ti—IF-nanoparticles, Ni—Co—IF-nanoparticles, Co—Cr—IF-nanoparticles. The coating material may comprise (i) Ni—P, Co—P, Co—B, Ni—B, Co—Ni, Cr—Co, TiN, TiON, Ti, Ni—Co, Co—Cr alloys and (ii) IF—$WS_2$ or IF—$MoS_2$ nanoparticles. In some embodiments, the metal or metal alloy comprises cobalt, nickel, chromium-cobalt, Ti, TiN, titanium-based alloy, nickel-based alloy, cobalt-based alloy. The present invention uses nanoparticles of layered compounds, like $MoS_2$ and $WS_2$, having hollow closed-cage structures and known as fullerene-like (IF) and inorganic nanotubes (INT) which can be synthesized in macroscopic amounts. The incorporation of the nanoparticles in metallic films (via wet deposition methods or via physical vapor deposition techniques) endows such metallic films self-lubricating behavior, i.e. low friction and wear. The term "fullerene-like (IF) nanostructures" or "inorganic fullerene-like (IF) nanostructures" within the context of the present invention covers hollow nanoparticles of transition metal chalcogenides and dichalcogenides, made up of single or multi-layers and having structures such as spheres, tubes, nested polyhedra, onion-like and the like.

In some embodiments, the IF nanostructures are made of metal chalcogenide or metal dichalcogenide.

A "transition metal" includes all the metals in the periodic table from titanium to copper, from zirconium to silver and from hafnium to gold. Preferably, the transition metals are selected from Mo, W, V, Zr, Hf, Pt, Pd, Re, Nb, Ta, Ti, Cr and Ru. A "chalcogen" as used herein refers to S, Se or Te. The metal chalcogenides and dichalcogenides are preferably selected from $TiS_2$, $TiSe2$, $TiTe_2$, $WS_2$, $WSe_2$, $WTe_2$, $MoS_2$, $MoSe_2$, $MoTe_2$, $SnS_2$, $SnSe_2$, $SnTe_2$, $RuS_2$, $RuSe_2$, $RuTe_2$, GaS, GaSe, GaTe, InS, InSe, $HfS_2$, $ZrS_2$, $VS_2$, $ReS_2$ and $NbS_2$. More preferably, the metal chalcogenides and dichalcogenides are selected from $WS_2$ and $MoS_2$.

In some embodiments, the coating of a material comprising metal or metal alloy and inorganic fullerene-like (IF) structures or a composite containing such nanostructures comprises inorganic fullerene-like (IF) structures or a composite containing such nanostructures in a range of about 1 wt % to 15 wt %.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 3A-3D represent an XRD experiment of an endodontic file which is being strained by a combined clamping/twisting force. In particular.

DETAILED DESCRIPTION OF EMBODIMENTS

Figure 2A:
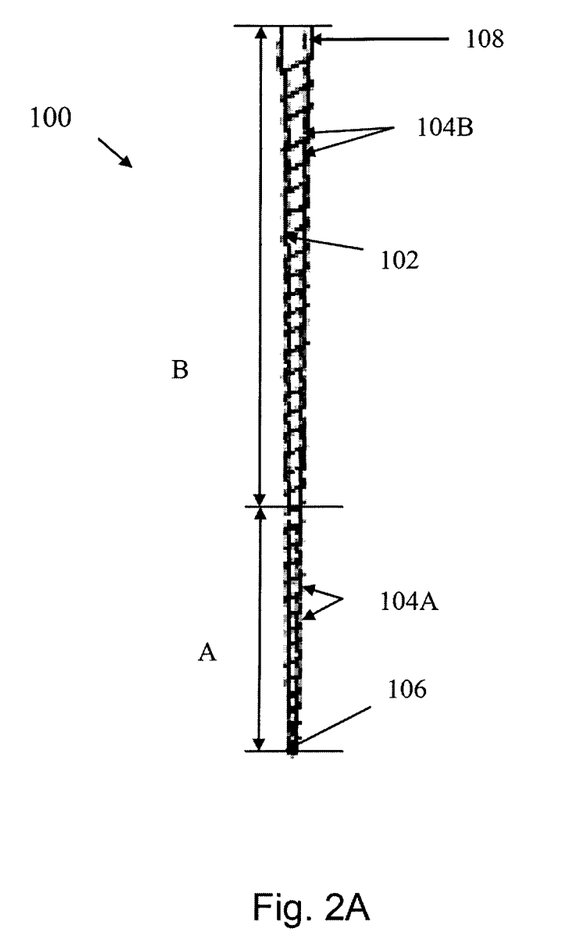
FIG. 2A is a schematic representation of the novel configuration of the EF of the present invention.
Figure 2B:
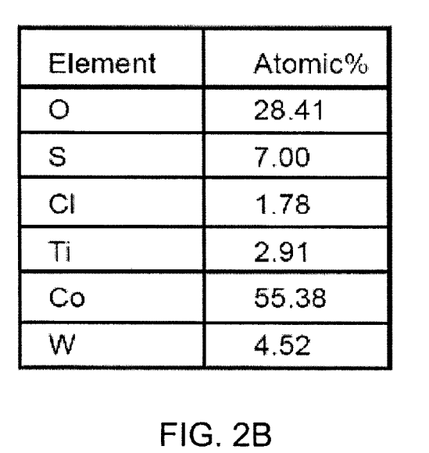
FIGS. 2B-2E represent an EDS analysis of the coated file (FIG. 2B) and SEM images (FIGS. 2C-2E) of a file coated with Co/IF film.
Figure 2C:
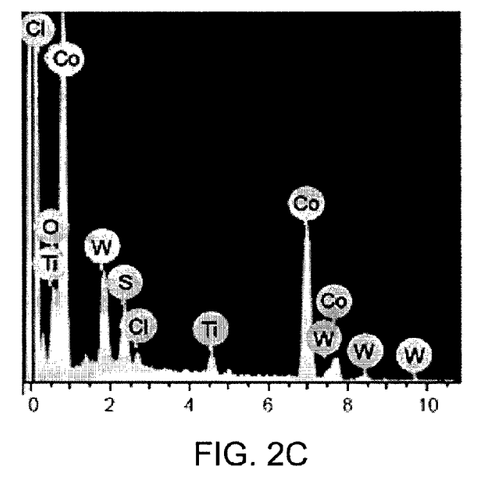
Figure 2D:
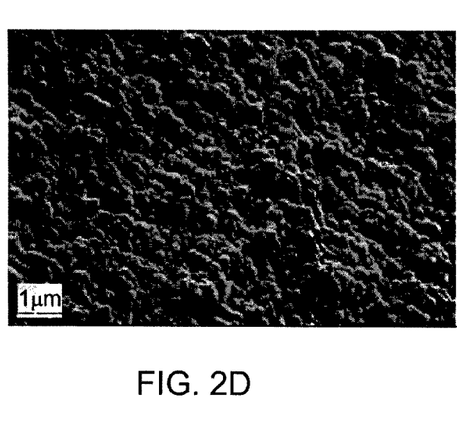
Figure 2E:
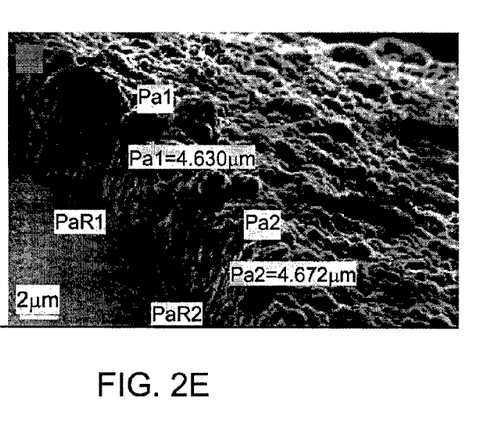

Reference is made to FIG. 2A showing a novel endodontic file 100 for root canal treatment according to the teaching of the present invention. The endodontic file 100 comprises an elongated integral body 102 formed with blades 104 defining a rotatable screw made member. The member is made of a shape memory and superelastic material composition, has a distal end 106 for penetration into the root canal and a proximal end 108 through which a force is applied to the body 102 to enable the penetration of the distal end 106. The screw member is formed with a coating of a material comprising cobalt, nickel, chromium-cobalt, Ti, TiN, titanium-nickel alloy, nickel-cobalt alloy and fullerene-like nanostructures with a predetermined non-uniform distribution of the coating material along the member. The non-uniform distribution is selected for reducing failure rate of the file and file fracture under the application of the force through the proximal end 108. The force applied to the body 102 includes an apical force pushing the file forward and torque responsible for the rotary motion of the file. The non-uniform distribution of the coating material may be selected such that a portion A of the member at the distal end is uncoated, and a remaining portion B of the member is coated. Alternatively, the non-uniform distribution of the coating material may be selected such that the blades 104A within a portion A of the screw member at the distal end are uncoated, while a remaining portion B of the member is coated.

In this connection, it should be understood that the portion A of the member at the distal end is the leading part of the file 100. When inserted within the root canal, portion A run into the material that has to be removed from the canal and drill the material out. Therefore portion A has a high friction coefficient. On the contrary, portion B should have a substantially reduced friction coefficient reducing thereby the file tendency to go through the stress related phase transformation. Reducing the friction between the file (and also the drilling chips) with the walls of the canal, reduce the stress applied on the file and its fatigue, thereby minimizing the rate of file failures.

Figure 2F:
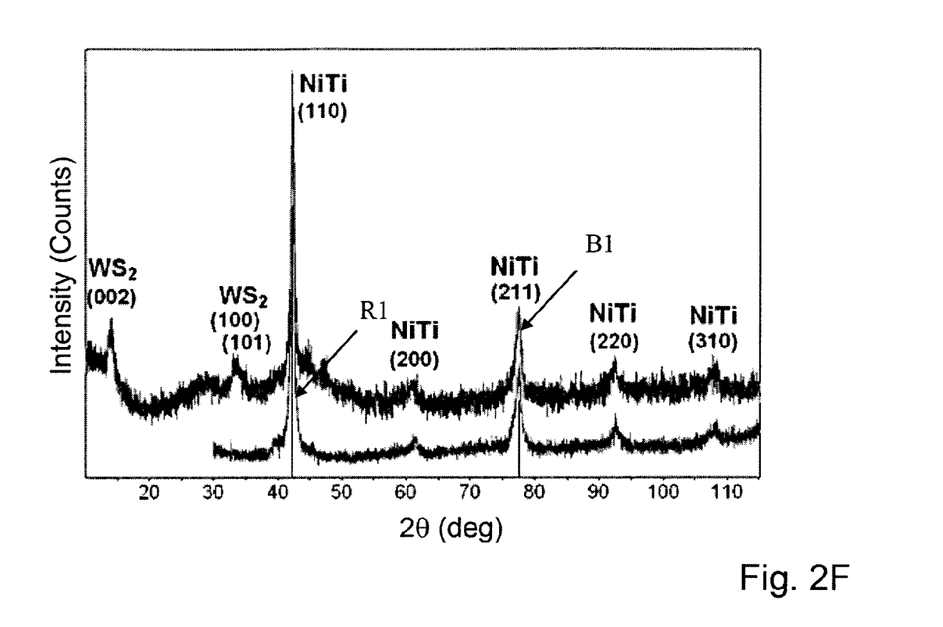
FIGS. 2F-2G represent an XRD pattern of a coated (B1 curve) and an uncoated file (R1 curve)

In some embodiments, the length of the portion A at the distal end is about ⅓ of the entire screw member (A+B). Reference is made to FIGS. 2B-2G showing an Energy-dispersive X-ray spectroscopy (EDS) analysis (2B) and SEM images (2C-2E) of an endodontic file coated with a Co film impregnated with IF—$WS_2$ nanoparticles (Co/IF). The coating was prepared, at a current density of 12 mAcm$^{-2}$, for a period of 6 min. The nanoparticles appear as surface bulges. The thickness of the films was found to be roughly proportional to the deposition time (about 0.8 μm/min). It appears from the EDS analysis (20 keV beam) that the coating contains typically 5-8 at % of IF—$WS_2$ nanoparticles. The XRD pattern of a coated and an uncoated endodontic file is shown in FIG. 2F. FIG. 2F represents an XRD pattern of a coated (B1 curve) and an uncoated file (R1 curve). The low angle peaks show the presence of IF—$WS_2$. An S1 Protaper® endodontic file commercialized by Dentsply was used in all experiments. The coating was performed by means of electrodeposition, by a protocol similar to those of Friedman et al [22]. The coating was evaluated using chemical and structural characterization methods using a scanning electron microscopy (SEM) model LEO-Supra™ 55vp commercialized by Zeiss, an X-ray energy dispersive spectrometry (EDS) (INCA energy, Oxford, England) and an X-ray diffraction (XRD) (model D-MAX/B, Rigaku, Japan).

The XRD pattern shows that the coating process did not alter the file's phase composition and the Ni:Ti ratio remained unchanged (51:49). Moreover, the IF—$WS_2$ nanoparticles are omnipresent in the coating.

Figure 2G:
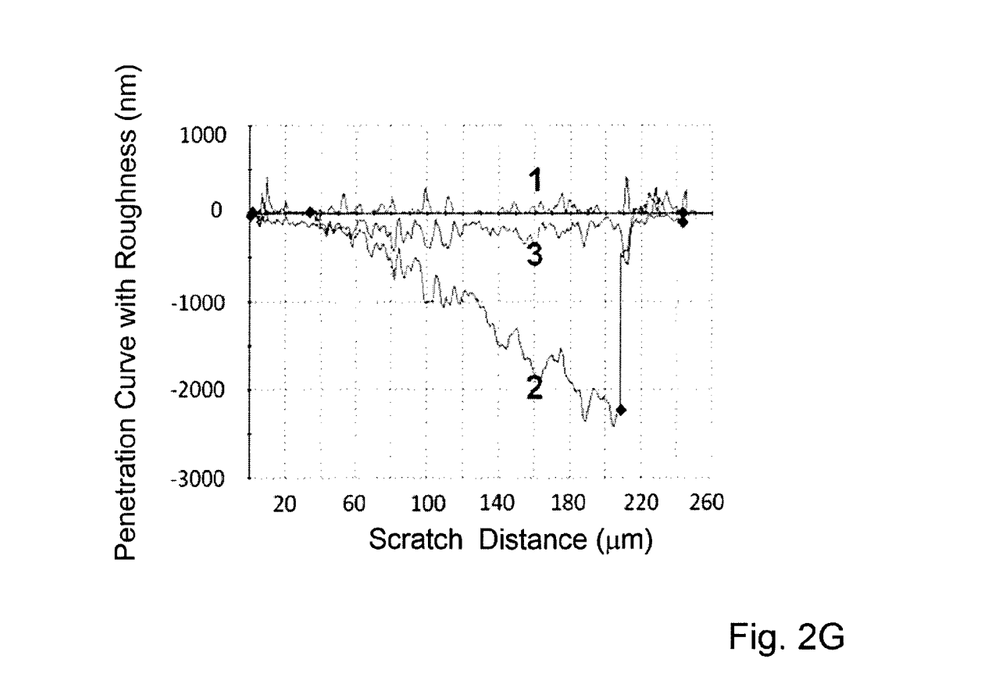

Reference is made to FIG. 2G representing a Nanoindenter-based scratch test on a Co/IF-coated file. The scratching load was linearly ramped from 0 to 30 mN over scratch distance of 200 microns. Curve 1 represents the initial profile, curve 2 represents the profile while loading/scratching, and curve 3 represents a final profile used to estimate elastic recovery/plastic deformation. The scratch test of FIG. 2G showed an almost complete recovery after the stress has been removed, indicating good elasticity of the file and adhesivity of the coating as detailed below. The adhesion of the coating was evaluated using scratch test (Nanoindenter, model XP, MTS) with a spherical diamond indenter tip, at a maximum scratch load of 30 mN, scratching at a velocity of 7 μm/sec. The traces in FIG. 2G show that up to these loads, there is no delamination or failure of the film, and the deformation is mostly elastic, with a plastic component well below 10%.

The XRD (TTRAX-Rigaku) test was performed using the torsional device. The XRD test was done while twisting a coated and an uncoated file. The gripping of the file was accomplished by fixing it between two stainless steel (440C) metal pieces forced with four metal springs. These four identical springs, with a spring constant of 39.6 N/mm were used for applying a measured uniaxial force on the file. They were tightened by a top screw which pushed down a plate fixed to the springs. The force applied by the spring is proportional to its length L which was accurately measured with a caliper. The insertion length of the file—d was also measured by a digital caliper (see inset with exploded view of the tightened file in FIG. 3A). The X-ray beam was focused just outside the stressed zone (marked by an arrow on the exploded view). To simulate the application of the torque in the root canal, the file was twisted and the torsion angle was read using a compass. The insertion length d was 9.1 mm in this series of experiments. At the beginning of every session of experiments, the length of each of the four springs was accurately measured to verify that they were not plastically deformed.

Reference is made to FIGS. 3A-3D illustrating an XRD experiment of an endodontic file being strained by a combined clamping/twisting force. A custom-made torsion device illustrated in FIG. 3A has been manufactured to measure an X-ray diffraction (XRD) pattern of the NiTi file while being tightly gripped by the metal supports of the torsion device and twisted. The torsion device was fabricated for torsion experiments of the endodontic file in order to allow measuring the diffraction pattern of an endodontic file while being subjected to combined rotational and loading strains/stresses. This experiment is not intended to directly simulate the rotation of the file inside the root canal, but it nonetheless serves to take account of some of the salient features of this operation and it bears some similarity to the real situation when the torque is exerted on the file in a constricted canal.

The spring having a length L holds the file in place. The file is inserted between the gripping metal plates in the insertion depth d. The values of d and L were kept uniform throughout the experiments. The combined force applied by the springs was 475.2N. Furthermore, the file was twisted at an angle of 100°. The torsional force component—or torque was estimated to be about 0.22 N*cm (uncoated file). In the inset with exploded view of the tightened file in FIG. 3A, the arrow points to the place where the X-ray beam was focused.

Figure 3A:
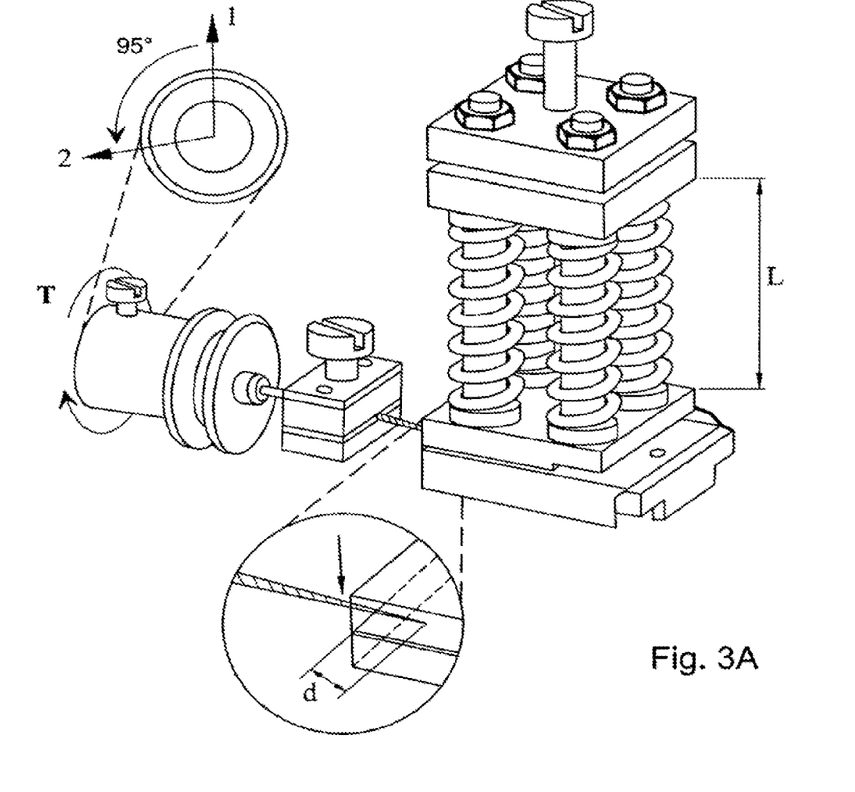
FIG. 3A represents a torsion device used for the torsion experiments of the endodontic file.
Figure 3B:
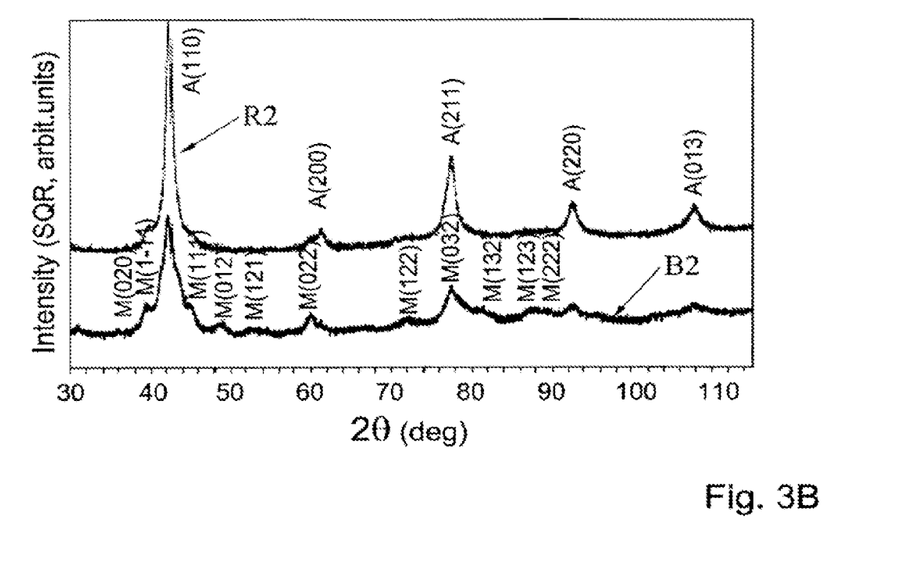
FIG. 3B represents a XRD pattern of the twisted file showing the austenite-martensite phase transformation.

FIG. 3B shows the XRD pattern (wide scan) of the twisted file showing the austenite-martensite phase transformation. While the (gripped) untwisted file consists mainly of austenite (R2 curve) [12, 14, 15], the twisted file (B2 curve) shows stress-induced phase transformation into martensite. The XRD pattern of the clamped untwisted file shows that it consists mainly of an austenite phase (the R2 curve). Twisting the file while being gripped produces a phase change for majority of the NiTi crystallites in the file into the (detwinned) martensite (B2 curve).

Figure 3C:
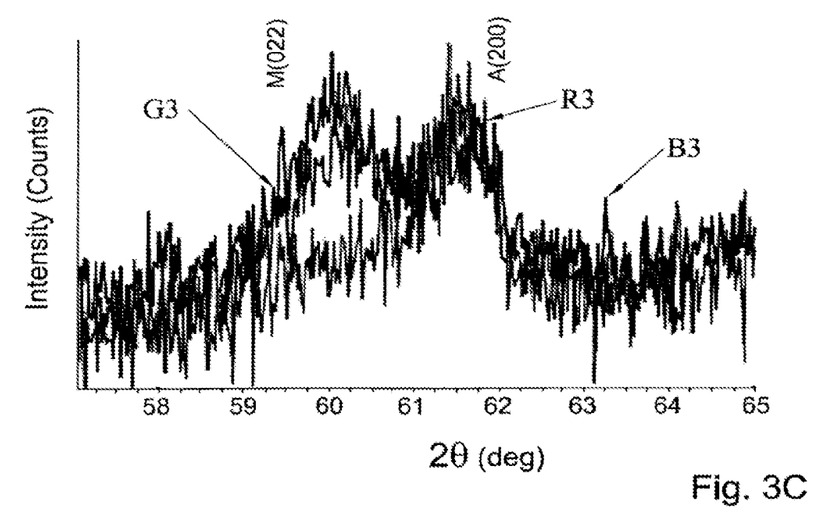
FIG. 3C represents XRD patterns of coated and uncoated files near 60°.

FIG. 3C compares the XRD pattern (narrow scan) of a coated (B3 curve) and uncoated (R3, G3 curves) files gripped by the torsional device of FIG. 3A. The XRD was focused around $2\theta=60°$ angle, where the austenite-martensite peaks are close but still distinguishable from one another. The files were twisted to the same degree, before the XRD was performed. An uncoated file was measured first (R3 curve), followed by a coated file (B3 curve), and then a repeated test of the uncoated file (G3 curve). The coated file appears to consist mainly of an austenite phase (no observed phase transformation) under strain, while the uncoated file transforms into martensite (left peak). Under a gripping force (475.2 N) and 100° twist angle, the austenitic-martensitic phase transformation is clearly seen on the uncoated file as shown in FIG. 3C. In contrast, the coated file does not show this phase transformation under the same combination of uniaxial and torsional strains. In fact, when mounting the coated file at the same gripping force (475.2 N), no phase transformation occurs, regardless of the twisting angle. These results indicate that the Co/IF coating leads to a substantial reduction in friction between the coated file and the surfaces of the gripping metal pieces reducing thereby the specimen tendency to go through the stress related phase transformation. It should be noted that these experiments were repeated many times with no observable damage to the file or the coating or its delamination from the file surface.

Figure 3D:
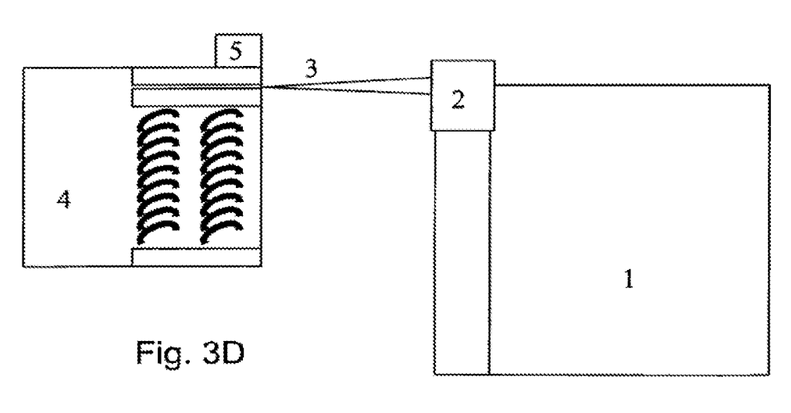
FIG. 3D represents a schematic configuration (top view) and image (bottom view) of a torque measuring platform.

FIG. 3D represents a schematics illustration (top view) and an image (bottom view) of the torque measuring platform. In the figure, 1 represents the apical movement motor, 2—the endodontic designated torque motor, 3—the endodontic file, 4—the sample and 5—the torque sensor. The friction reducing effect of the Co/IF coating was evaluated using an endodontic designated torque-control motor mounted on a rig. The platform was composed of a rotational motor 2 (Dentsply, Tulsa dental, ATR Tecnika Digital Torque Control) and a torque sensor 5 (CMSS 60, Eddy Probe).

During the initial static torque measurements, the file was held between the two metal plates (stainless steel 440C) partially tightened by a force of 475.2N, provided by the four springs. The length d of the file gripped between the plates was 8.9 mm, permitting forced rotation of the file within the partially tightened metal plates. The file rotating motor was set to a frequency of 100 rpm. The amount of torque required to achieve 100 rpm is proportional to the friction coefficient of the file, therefore giving an indirect way of measuring this parameter. Comparing the friction coefficient of coated and uncoated files, it was shown that the torque applied in order to overcome the static friction was 0.9 N*cm in the case of the uncoated file and 0.27 N*cm for the Co/IF coated file. This three-fold reduction is significant in relation to the force required for drilling. In this connection, it should be understood that if the screws are tightened with relative low force, the EF can rotate and suffer fatigue until failure. If the screw is tightened with high force, the EF is unable to move and breaks almost instantaneously upon applying a torque. This situation is equivalent to incidental failure, when the file goes to a blocked canal and too much force is applied on it. In both cases, the non-uniform distribution of the coating being made of metal-IF films led to much improved performance and delayed failure time.

A torque rig was constructed to simulate the irreversible stress produced on a functional file. The torque rig was used in order to test the failure of a coated file, compared to an uncoated one. The first experiment was performed using a high gripping force (633 N) and low motor frequency (80 rpm). The last 6 mm of the file's distal end (d=6, FIG. 3D) were held between the steel boards (stainless steel 440C). The applied load (633 N) was sufficiently high to cause separation (breakage) of the file after some measured time. In the second experiment (fatigue induced failure) the gripping force was lowered into (110.9 N L=8.79 mm), so that the file could rotate forward (0.2 s) and backwards (0.1 s) between the metal pieces. The working length of the file d was 4.4 mm.

Nanoindentation can be used as a tool for evaluating the internal stress and fatigue of a NiTi file following clinical work. Generally, NiTi substrate presents a bimodal distribution of the elastic modulus and hardness. Crystallites consisting mostly of the martensite phase exhibit Young's modulus of between 20 to 50 GPa, while austenite domains show values of 40 to 90 GPa [18]. The results of the mechanical measurements reported in the literature vary greatly with the specific testing conditions, applied stress and the temperature. Moreover, the volume fraction of the martensite may increase while applying the stress by the nanoindenter tip, which may explain the scattering in the experimental data. The nanoindentations (Nanoindenter, model XP, Agilent) were preceded by a preliminary in-situ topographical scan at a range of $40*40$ $\mu m^2$, in order to evaluate the surface roughness of the specimen and precisely choose indentation locations. The endodontic file was glued to a sample holder, after cutting the handle part up until the first spiral. The indentation tests were performed 25 times on each specimen. The locations for the nanoindentation experiments were randomly distributed on the two last spirals of the file using a Berkovich tip (with a radius of curvature of about 100 nm) and a penetration depth of 350 nm.

Figure 4A:
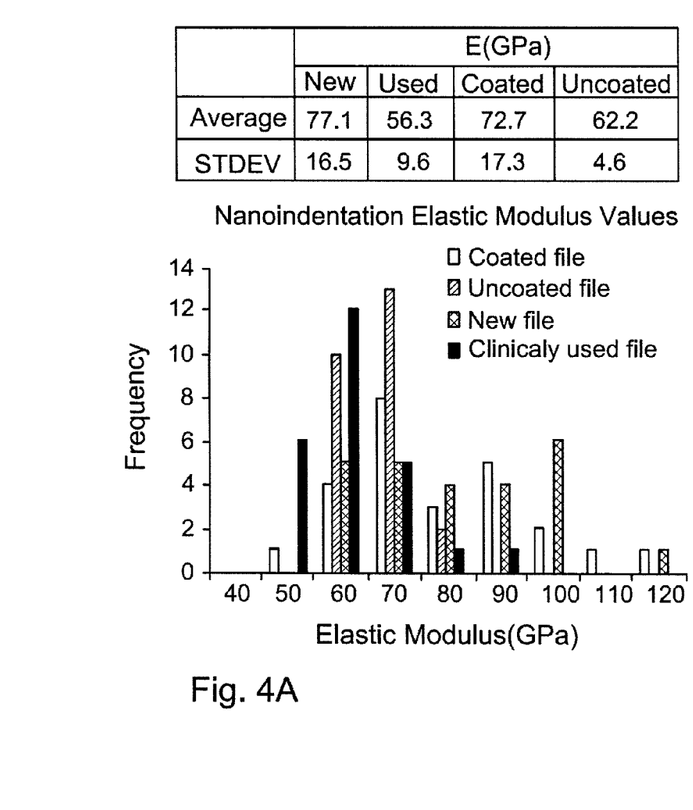
FIGS. 4A-4B represent modulus (E) and hardness (H) values obtained through nanoindentation experiments for: clinically used (1); unused files (2); coated file subjected to stress using the torque platform (3); uncoated file subjected to the same amount of stress as the coated one, using the torque platform (4)
Figure 4B:
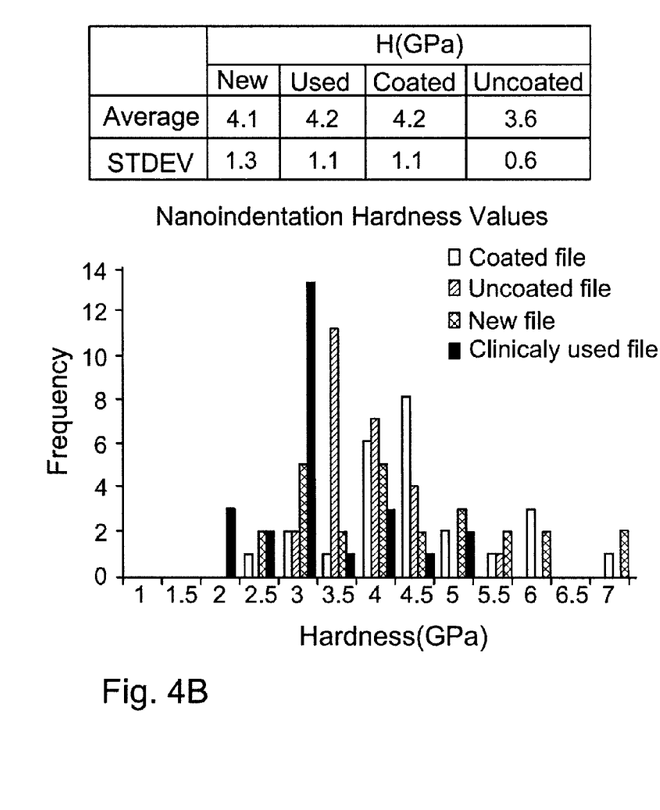

Reference is made to FIGS. 4A-4B illustrating a series of nanoindentation measurements of four different endodontic files (samples 1 to 4).

FIGS. 4A-4B represent the modulus (E) and hardness (H) values obtained through nanoindentation experiments for: unused files (1); clinically used files (2); coated file subjected to stress using the torque platform (3); uncoated file subjected to the same amount of stress as the coated one, using the torque platform (4). It should be noted that the analysis indicates that the uncoated file has suffered severe fatigue. The measurements were carried out on the files' tips, where the surface machining during production leads to substantial increase in the martensite phase at expense of the austenite and possibly also residual stress. The mechanical properties (elastic modulus and hardness) of file tips of two couples were compared: a fresh (pristine) file (1) and a clinically used file discarded from an endodontic practice (2), coated (3) and uncoated (4) files subjected to the same amount of work using the torque rig (FIG. 3D) were also measured. First, the elastic modulus (FIG. 4A) and hardness (FIG. 4B) of a fresh file (1) were compared to those of a used file (2), discarded from an endodontic practice. This clinically used file served for the shaping of five different root canals. The fresh file (1) shows a bimodal distribution with the two peaks centered around 90 and 60 GPa in the modulus. Moreover, the standard deviation (STDV) of the elastic modulus is very high in this case. The bimodal distribution of the modulus and strength (or the large STDV) suggests that martensitic and austenitic domains coexist in the sample interchangeably. The fresh file (1) thus shows a wide spread of elastic modulus and hardness values, as indicated by the relatively high standard deviations (STDV) of 16.5 GPa and 1.3 GPa respectively. It is suggested that the high spread is associated with the bimodal distribution, caused by the martensite and austenite domains, which coexist interchangeably in the sample file. On the other hand the results of the modulus (strength) of the used file (2) are single peaked and pushed to lower values. The STDV becomes much lower in this case, as well. The modulus and hardness results of the used file (2) are therefore much less spread out (STDV of 9.6 and 1.1 GPa), with the average elastic modulus shifted from 77.1 to 56.3 GPa. These observations could indicate a mechanical deterioration of the used files which is manifested as a low-stress related transformation [7]. Alternatively stated, these results can be attributed to fatigue-related martensite stabilization [7, 8].

In the next series of nanoindentation experiments, the Co/IF coated file (3) was compared to an uncoated file (4). Both files went through the torque measuring test (discussed above using the rig shown in FIG. 3D) prior to the present experiment and hence are believed to have suffered some fatigue. Indeed it is seen that, both files exhibited reduced average modulus and hardness compared with an unused file (1). Nevertheless, the reduction is much more significant in the uncoated file (4) as compared to the coated one (3). In fact, the coated file exhibits bimodal distribution with somewhat reduced values as compared to the unused file, indicative of a modest fatigue. The elastic modulus of the coated file exhibits a STDV which is significantly larger than that of the uncoated file (17.3 vs. 4.6 GPa), which may be indicative of the modest fatigue and retention of the mechanical properties of the file. Contrarily, the modulus and hardness of the uncoated file shows a single peak, at much lower values (mean values of 62.2 and 3.6 GPa, respectively) which are similar to those of the clinically used file. These results suggest that the uncoated file has suffered a great deal of fatigue during the torque measurements.

It should be understood that reducing the friction between the file (and also the drilling chips/swarf) with the walls of the canal, reduce the stress applied on the file and its fatigue, thereby minimizing the rate of file failures. The initial friction of the partially gripped file was measured using a torque measuring rig device of FIG. 3D. The amount of applied torque required to achieve 100 rpm is inversely proportional to the friction coefficient of the file, therefore giving an indirect estimate for this parameter. Here, a Co/IF coated file was compared to the uncoated file (the friction coefficient of NiTi substrates coated with Co alone was found to be very high [22] and was not studied here any further). The file was held by the two metal supports, which were not fully tightened (clamping force of 475.2 N) in order to allow forced rotation of the file. The applied torque went down from 0.9 N*cm in the case of the uncoated NiTi file to 0.27 N*cm for the Co/IF coated file. This experiment was repeated three times with three different pairs of coated and uncoated files showing very small variations in the measured values. These results indicate that the coating leads to a substantial reduction in the friction between the coated file and the metal support.

Figure 5A:
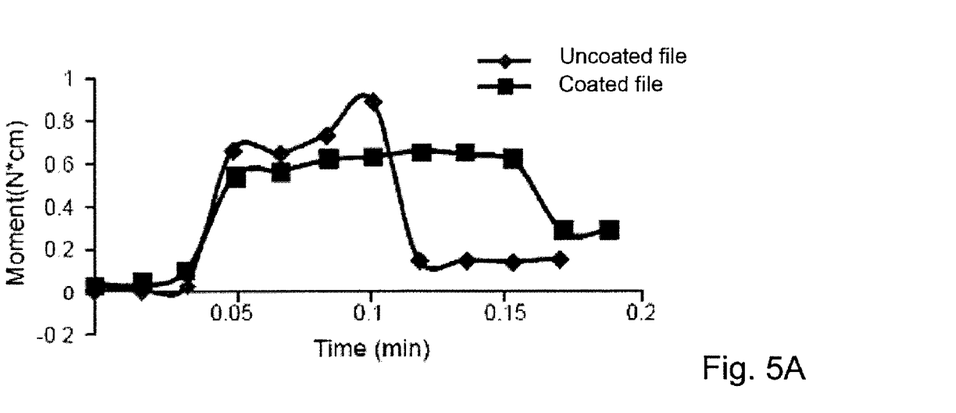
FIG. 5A represents an incidental torsional failure test of an uncoated file and a coated file.
Figure 5B:
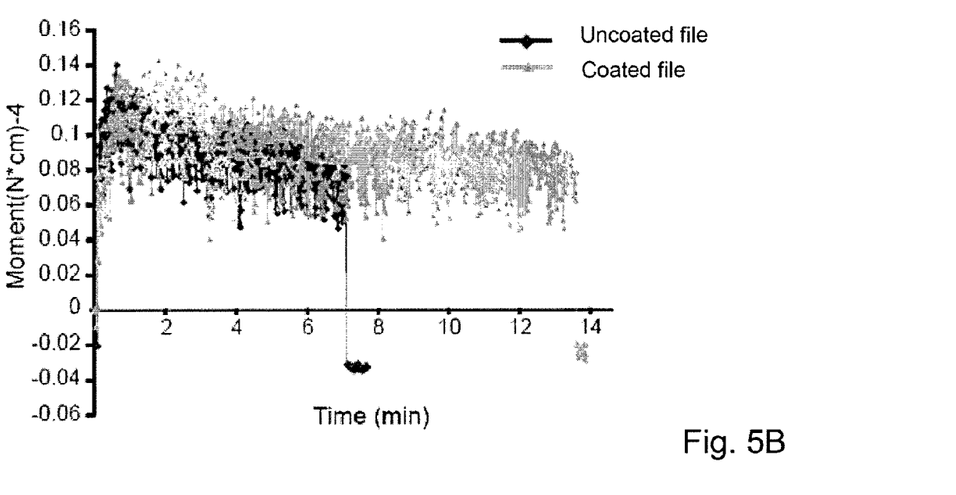
FIG. 5B represents fatigue induced torsional failure of a coated file and an uncoated file.

Reference is made to FIGS. 5A-5D illustrating rotation to failure experiments of the files performed on the platform of FIG. 3D. Two different situations were tested. In FIG. 5A, the clamping force applied on the tip was relatively high (633 N), simulating the taper lock (incidental) mode of failure. On the contrary, the clamping force of the tip in the experiment described in FIG. 5B was modest, which could lead to fatigue-related failure. In particular, FIG. 5A represents a time to incidental torsional failure test of an uncoated file and a coated file (see FIG. 3D for the experimental set-up). This failure mode, which is not rare in the practice, could also be ascribed to any other NiTi medical device (such as a guidewire), when the distal end of the device (the leading part) is subjected to the highest torque surpassing its yield strength. In these experiments, the applied orthogonal clamping force was high (633 N), i.e. the length of the springs—L was reduced. It is noticed that although the time to failure of both kinds of files was short, the separation of the coated file took twice as long on the average as compared to the uncoated file (6 s for a coated file vs. 3 s for an uncoated file). Moreover, the applied torque (maximal value of 0.88 N*cm) on the uncoated file during this test was higher than that applied on the coated one (0.62). These results are consistent with the results of the friction test, showing that effect of the file coating is to reduce the applied torque. These results also suggest that during clinical work the coated files could exhibit lower incidental failure probability in constricted canals, where locking of the file is apparent. FIG. 5B shows the results of an (almost free-clamping force) rotation experiment of a file until failure. A fatigue induced torsional failure of a coated file and an uncoated file is represented. The figure shows the torque applied on an uncoated and on a Co/IF coated file, while twisting back and forth between two metal pieces. The files were held at a relatively low force of 110.9 N. The uncoated file failed after 7.1 min while a coated file separated after 14.1 min. Here, the file rotates back and forth—0.20 s in forward motion and then 0.10 s in reverse motion until failure leading to fatigue-related failure. This mode of failure is further evidenced by the presence of striations (shear bands due to martensite domains—see FIGS. 5C-5D) on the surface of the fractured area. The striations appear beneath the corners of the files where load is maximum during rotation. The separation is indicated as a sudden reduction in the torque. While the uncoated files failed after 6.3-7.2 min, the coated files failed after 14-19 min (3 files for each set of experiments).

Figures 5C, 5D:
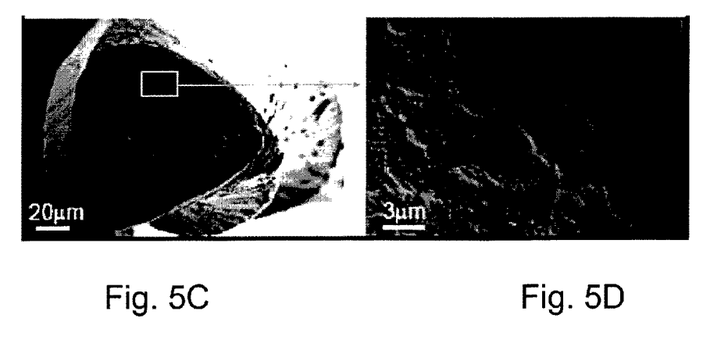
FIGS. 5C-5D are SEM images of the uncoated file subjected to torsional fatigue failure (of FIG. 5B)

FIGS. 5C-5D show head-on SEM images of a broken (uncoated) file subjected to torsional fatigue-induced failure (see FIG. 5B for details). On the enlarged image fatigue striation (shear bands) is shown, indicating that the breakage was related (at least in part) to fatigue. The presence of striations (shear bands due to martensite domains) on the surface of the fractured area is indicative of fatigue-based failure [19, 20, 21]. The striation zones appear under the corners of the file's triangular cross-section (FIGS. 5C-5D). This indicates that, as expected also from the stick-slip behavior (see below FIGS. 5E-5H), the torque is not uniformly distributed on the circumference of the file. Therefore the striations nucleate at the corners close to the file surface, where the file-canal-wall interaction is the strongest. Consequently, reducing the torque and making it more uniformly distributed on the coated file surface lead to a time-delay for nucleation of the striations which are associated with irreversible changes and fatigue.

Therefore, it was shown that the EFs of the present invention experience a selectively distributed friction, phase transformation and less mechanical deterioration as compared to their uncoated counterparts. This suggests that the EFs of the present invention are less susceptible to breakage under work related strain, as occurs during root canal treatment. In addition, the selectively distributed friction and subsequent torque allows the use of NiTi EFs under conditions currently considered too risky and complicated. The proposed selective coating may be applicable to a wide range of NiTi-based technologies and medical applications, and has a favorable influence on the performance and lifetime of NiTi devices.

Figure 5E:
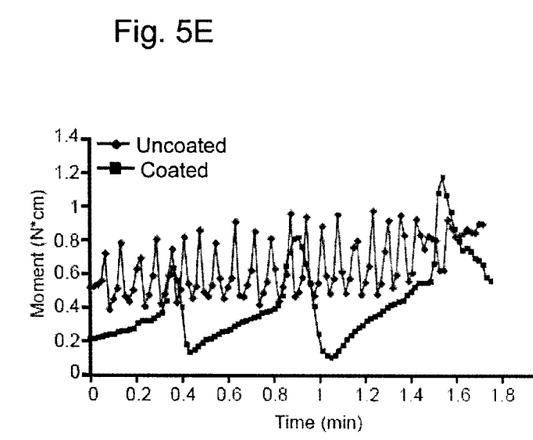
FIG. 5E represents a dynamic torque applied by an endodontic file while drilling into a constricted hole made in a PVC substrate.

After establishing the lubricating ability of an IF-nanoparticles coating, the torque applied onto coated and uncoated files during simulated clinical work was tested. The files drilled into preformed holes of 0.35 mm, at a rotation speed of 250 rpm, using the torque rig of FIG. 3D. Pre-drilled holes were used in order to keep a standard diameter. The torque of a coated and an uncoated file, while drilling an opening (preformed holes) of 0.35 mm in a PVC substrate was measured. The results of the dynamic torque tests, which examine the drilling ability of coated and uncoated files (FIG. 5E), show that the coated files exhibited smaller torque values. FIG. 5E represents a dynamic torque applied by an endodontic file while drilling into a constricted hole (0.35 mm in diameter and 5 mm deep) made in a PVC substrate. The graphs of torque (moment) over time shown in the figure represent a single course of entering and re-entering the simulated canal. The oscillatory behavior of the graph is attributed to the stick-slip phenomenon, which is typical of high friction scenarios (boundary lubrication). The torque applied by the coated file on the wall is substantially lower than that applied by the uncoated file for most of the drilling time. The final dimensions of the holes are about 10% smaller for the coated vs. the uncoated files. Therefore, probably due to lower friction with the canal, the coated file creates a smaller drilling hole. The coated file thus shapes the canal more accurately, keeping the contour of the canal more precisely than an uncoated file.

By comparing the stick-slip behavior of the coated file and the uncoated file during the drilling test, one can see that the oscillation frequency is much higher in the case of the uncoated file. This implies that the gripping of the file, which is the base of the stick-slip phenomenon, causing the increase in the torque (the maximum in the oscillating stick-slip behavior), occurs more often than in the case of the uncoated file. Since the stick-slip phenomenon is typical of high friction scenarios, it is likely that the reduced frequency oscillation of the coated file is the result of the lower friction encountered in this case.

Figure 5F:
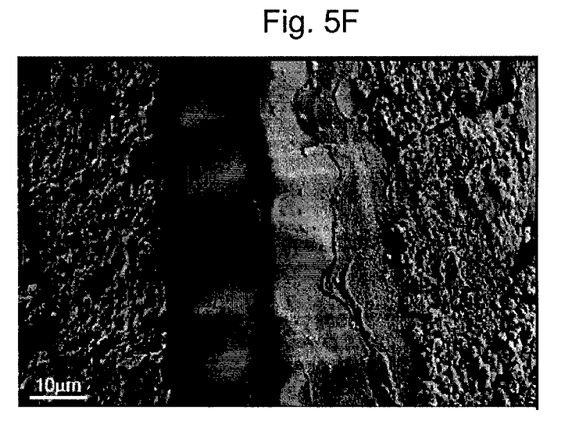
FIGS. 5F-5H are SEM images of the coated file after the drilling test.
Figure 5G:
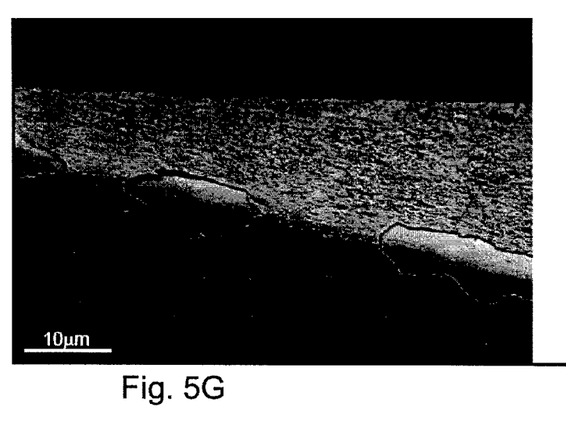
Figure 5H:
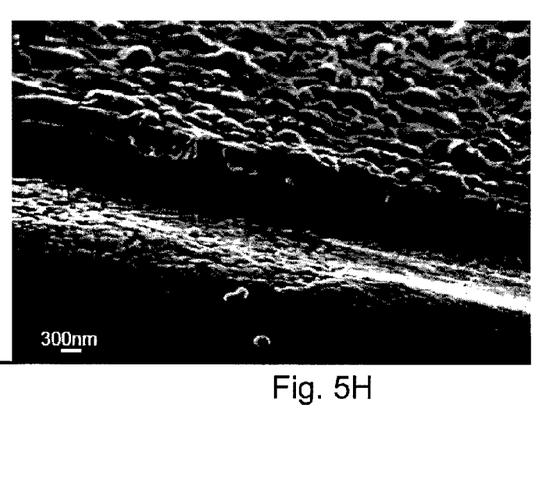

FIGS. 5F-5H are SEM images of the coated file after the drilling test. It should be noted that the wear of the coating is mainly in the area of the reamers. The same torque rig used in the initial torque test was employed in this experiment. The rotation speed was 250 rpm and the apical movement was 0.02 mm/s.

The maximal torque invested while drilling the coated file into the canal is the same as or even higher than that of an uncoated one. As could be expected, the slope of the graph of a coated file is less steep than in an uncoated file.

The stick-slip phenomenon of the uncoated file reflects the interaction of the triangularly-shaped file with the walls of the hole (see FIG. 5C). The absence of high frequency stick-slip phenomenon and lower torque indicates a smoother penetration of the coated file and consequently a reduced fatigue. This is also vindicated by the size and shape of the pore openings. Indeed, the diameter of the drilled pore size is found to be 10% smaller on the average for the coated as compared to the uncoated file. Furthermore, the cross-section of the pore obtained by the coated file has a circular shape as compared to a rhomobohedral shape of the uncoated pore. Improving the NiTi instrument ability to remain concentric inside the canal by Co/IF coating, as suggested by the results of this study, might further reduce procedural unfavorable outcomes. The proposed coatings are likely to have a favorable influence on the performance and lifetime of other medical and general NiTi-based technologies.

The invention claimed is:

1. An endodontic file for root canal treatment, the endodontic file comprising an elongated body having a length and having a distal end configured to first penetrate into the root canal when in use, and a proximal end to which a force is applied to allow penetration of the distal end into the root canal when in use, said elongated body being configured as a rotatable screw member made of a shape memory and superelastic material composition, and having helical screw cutting blades arranged with core spaces between the blades, wherein the helical screw cutting blades and the core spaces therebetween, within a proximal portion of the elongate body, are coated with a friction-reducing coating comprising nanostructures of (a) metal or metal alloy and (b) inorganic fullerene-like (IF) nanoparticles or a composite containing such IF nanoparticles, while the helical screw cutting blades of the elongated body are uncoated within a distal portion of the elongate body, wherein said distal portion is distal to said proximal portion, the elongated body thereby having a non-uniform distribution of the friction-reducing coating.

2. The endodontic file of claim 1, wherein said distal portion has a length of about ⅓ of the length of the elongated body.

3. The endodontic file of claim 1, wherein said shape memory and superelastic material composition is selected from the group consisting of NiTi and stainless steel.

4. The endodontic file of claim 1, wherein said coating has a thickness of between 0.3 micron and 10 microns.

5. The endodontic file of claim 1, wherein the IF nanoparticles or the composite containing the IF nanoparticles reduce friction between the file and the canal.

6. The endodontic file of claim 1, wherein said coating is selected from the group consisting of Ni—P—IF-nanoparticles; Co—P—IF-nanoparticles; Co—B—IF-nanoparticles; Ni—B—IF-nanoparticles; metal film containing IF-nanoparticles; polyurethane, polypropylene or epoxy containing IF-nanoparticles; a sol-gel glass containing IF-nanoparticles; Co—Ni—IF-nanoparticles; Cr—Co—IF-nanoparticles; TiN-IF-nanoparticles; TiON—IF-nanoparticles; Ti—IF-nanoparticles; Ni—Co—IF-nanoparticles; and Co—Cr—IF-nanoparticles.

7. The endodontic file according to claim 4, wherein, in said coating, said metal or metal alloy is selected from the group consisting of Ni—P, Co—P, Co—B, Ni—B, Co—Ni, Cr—Co, TiN, Ti, TiON, Ni—Co, and Co—Cr alloys and said IF nanoparticles or said composite containing said IF nanoparticles are selected from the group consisting of IF—$WS_2$ and IF—$MoS_2$ nanoparticles.

8. The endodontic file of claim 1, wherein said IF nanoparticles are made of metal chalcogenide or metal dichalcogenide.

9. The endodontic file of claim 1, wherein said IF nanoparticles are made of $TiS_2$, $TiSe_2$, $TiTe_2$, $WS_2$, $WSe_2$, $WTe_2$, $MoS_2$, $MoSe_2$, $MoTe_2$, $SnS_2$, $SnSe2$, $SnTe_2$, $RuS_2$, $RuSe_2$, $RuTe_2$, GaS, GaSe, GaTe, InS, InSe, $HfS_2$, $ZrS_2$, $VS_2$, $ReS_2$ or $NbS_2$.

10. The endodontic file according to claim 4, wherein said IF nanoparticles or said composite containing said IF nanoparticles comprise IF—$WS_2$ or IF—$MoS_2$ nanoparticles.

11. The endodontic file of claim 1, wherein said coating comprises IF nanoparticles or a composite containing such IF nanoparticles in a range of about 1 wt % to 15 wt %.

12. The endodontic file of claim 1, wherein said metal or metal alloy comprises cobalt, nickel, chromium-cobalt, Ti, TiN, titanium-based alloy, nickel-based alloy, or cobalt-based alloy.

13. The endodontic file of claim 1, wherein said non-uniform coating is electrodeposited along said member.

14. The endodontic file of claim 1, wherein the core spaces between the uncoated blades of the distal portion of the elongated body are coated with said friction-reducing coating.

15. The endodontic file of claim 1, wherein the core spaces between the uncoated blades of the distal portion of the elongated body are also uncoated, such that all of the distal portion is uncoated by said friction-reducing coating.

16. An endodontic file for root canal treatment, the endodontic file comprising an elongated body having a length and having a distal end configured to first penetrate into the root canal when in use, and a proximal end to which a force is applied to allow penetration of the distal end into the root canal when in use, said elongated body being configured as a rotatable screw member made of a shape memory and superelastic material composition, and having helical screw cutting blades arranged with core spaces between the blades, wherein the core spaces between said cutting blades, within a distal portion of the elongate body, are coated with a friction-reducing coating comprising nanostructures of (a) metal or metal alloy and (b) inorganic fullerene-like (IF) nanoparticles or a composite containing such IF nanoparticles, while the blades of the elongated body are uncoated within the distal portion in which the core spaces are coated by the coating, the elongated body thereby having a non-uniform distribution of the friction-reducing coating.

* * * * *